United States Patent [19]

Hobson et al.

[11] Patent Number: 4,618,728
[45] Date of Patent: Oct. 21, 1986

[54] WATER AIDED CATECHOL ETHERIFICATION

[75] Inventors: Philip B. Hobson, Trenton; Robert E. Keay, Stockton, both of N.J.

[73] Assignee: FMC Corporation, Philadelphia, Pa.

[21] Appl. No.: 704,434

[22] Filed: Feb. 22, 1985

[51] Int. Cl.$^4$ ............................................. C07C 41/16
[52] U.S. Cl. ..................................................... 568/652
[58] Field of Search ......................................... 568/652

[56] References Cited

U.S. PATENT DOCUMENTS

| | | | |
|---|---|---|---|
| 2,362,479 | 11/1944 | Gibbs | 260/800 |
| 3,274,260 | 9/1966 | Levy et al. | 260/613 |
| 3,474,171 | 10/1969 | Scharpf | 424/285 |
| 3,927,118 | 12/1975 | Ozretich | 260/613 |
| 4,250,333 | 2/1981 | Rakoutz | 568/652 |
| 4,252,985 | 2/1981 | Rakoutz | 568/652 |
| 4,321,204 | 3/1982 | Büttner et al. | 260/346 |
| 4,390,733 | 6/1983 | Campolmi et al. | 568/652 |
| 4,420,642 | 12/1983 | Franko-Filipasic | 568/652 X |
| 4,465,868 | 8/1984 | Maekawa et al. | 568/652 |

FOREIGN PATENT DOCUMENTS 92102 10/1983 European Pat. Off. .
173437 8/1979 Hungary .

Primary Examiner—Bernard Helfin
Attorney, Agent, or Firm—William Schmonsees; H. Robinson Ertelt; Robert L. Andersen

[57] ABSTRACT

A method is disclosed for facilitating selective etherification of catechol with methallyl chloride in the absence of an etherification catalyst, in which there is employed a solvent system comprising an aliphatic ketone and an etherification aiding amount of water.

4 Claims, No Drawings

WATER AIDED CATECHOL ETHERIFICATION

The present invention relates to a process for preparing 2-methallyloxyphenol, an intermediate in the preparation of carbofuran, a commercial insecticide. More particularly, the invention relates to a process for preparing 2-methallyloxyphenol from catechol and methallyl chloride in a mixed solvent system consisting of controlled amounts of water and an aliphatic ketone, thereby eliminating the need for etherification catalysts.

The reaction of catechol with methallyl chloride to produce 2-methallyloxyphenol is well known to those skilled in the art and has been the subject of considerable research effort because of difficulty in simultaneously achieving rapid reaction rate, high selectivity toward the desired products, and adequate conversion of catechol.

It is known in the art that catechol and other dihydroxyphenols may be etherified in a wide variety of organic solvents. U.S. Pat. No. 2,362,479 teaches refluxing hydroquinone and methallyl chloride in alcoholic potash. U.S. Pat. No. 3,274,260 teaches the alkylation of dihydric phenols with an alkyl halide, alkyl sulfate, or toluenesulfonate utilizing a large amount of water and an immiscible organic solvent such as benzene, alkyl benzenes, or halogenated hydrocarbons.

U.S. Pat. No. 3,474,171 and Hungarian Pat. No. 173,437 teach reaction of catechol with methallyl chloride in an aliphatic ketone such as acetone or methyl ethyl ketone. U.S. Pat. Nos. 3,927,118 and 4,250,333 teach the use of organic dipolar aprotic solvents, including amides, sulfones, sulfoxides, ethers and aromatic hydrocarbons, U.S. Pat. Nos. 4,321,204 and 4,390,733 teach the use of glycol monoalkyl ethers which have at least one free OH group and various other alcohols and polyalcohols.

It is also known that the reaction between catechol and methallyl chloride can be conducted in the presence of an organic solvent and water, but only in the presence of a costly etherification catalyst such as potassium iodide or a phase transfer catalyst. Without such an etherification catalyst the reaction fails to proceed, is extremely slow, or, if forced, produces excessive undesired by-products. For example, in European Pat. No. 92102 and U.S. Pat. No. 4,252,985, the reaction is catalyzed with quaternary ammonium or phosphonium derivatives; and in U.S. Pat. No. 4,465,868, it is catalyzed with various iodides.

The present invention provides an economical and highly productive method for preparing 2-methallyloxyphenol from catechol and methallyl chloride. The method of this invention employs an aqueous/ketone solvent system which provides several distinct advantages over the processes of the prior art, including eliminating the need for costly etherification catalysts and their subsequent recovery, reaction rates which are equal to or better than those obtained with prior methods, and selectivity toward 2-methallyloxyphenol of about 90 percent or higher.

In accordance with the present invention there is thus provided a process for preparing 2-methallyloxyphenol in which catechol is reacted with methallyl chloride at a temperature in the range of 70° C. to 150° C. in the presence of a base selected from the group consisting of alkali metal carbonates, alkali metal bicarbonates, alkaline earth carbonates and alkaline earth bicarbonates, wherein said reaction is conducted in the absence of iodide and phase transfer etherification catalysts in the presence of a solvent system consisting of water and an aliphatic ketone having 4 to 8 carbon atoms, said solvent system containing from 0.35 to 1.85 moles of water per mole of catechol and being employed in an amount sufficient to provide a catechol concentration in the range of 5 to 50 percent by weight of the solvent system.

In the process of this invention, catechol conversion is limited from about 40 percent up to 70 percent preferably 45 percent up to about 55 percent in order to promote maximum selectivity toward 2-methallyloxyphenol and minimize formation of undesired by-products such as catechol diethers and/or products having a ring alkylation in the 4-position. These undesired by-products of the reaction cannot be cyclized to 2,3-dihydro-2,2-dimethyl-7-hydroxybenzofuran, the intermediate which is carbamoylated to form carbofuran. Small quantities of 3-methallylcatechol are present in the resulting product and may be readily converted to the 7-hydroxybenzofuran intermediate along with the 2-methallyloxyphenol.

The control of catechol conversion within the ranges provided above may be obtained by methods well known to those skilled in this art, for example, by utilizing from 0.4 to about 0.75 moles of methallyl chloride or base per mole of catechol, or by monitoring catechol consumption during the reaction and discontinuing the reaction when the desired consumption level has been reached. The unconverted catechol is readily recovered for recycle by methods well known to those skilled in this art, for example, by caustic extraction.

The reaction is conducted at a temperature which may be within the range of 70° C. to 150° C., advantageously 110° C. to 140° C. While the reaction temperature is not critical, the temperature selected will influence the reaction time required to obtain the desired degree of catechol conversion. It will also be apparent that if the solvent system employed has a boiling point below that of the selected reaction temperature, it will be necessary to conduct the reaction under pressure in order to obtain the desired temperature.

The bases for use in the invention are suitably alkali metal carbonates, desirably sodium or potassium carbonate, or a mixture thereof. When sodium and potassium carbonates are employed it is desirable to employ a substantial molar excess of sodium carbonate, thus the molar ratio of sodium carbonate to potassium carbonate may suitably be in the range of about 5 to 1 to about 20 to 1.

The amount of solvent utilized in the reaction may vary widely, but it is generally desirable to use sufficient solvent to provide a catechol concentration of from 5 to about 50, advantageously 15 to about 35, percent by weight based on the starting amounts of catechol and solvent.

The amount of water in the solvent system must be limited within a narrow range in order to achieve high selectivity toward 2-methallyloxyphenol and at the same time achieve highly beneficial reaction rates. If the water content of the solvent system is below about 0.3 mole per mole of catechol, the reaction rate becomes unacceptably low. Selectivity toward 2-methallyloxyphenol drops off markedly when more than about 1.9 moles of water per mole of catechol is employed in the solvent system, producing an unacceptable level of undesired byproducts. In accordance with the best mode for practicing the present invention, it is desirable to employ a solvent system containing from 1.1 to about 1.5 moles of water per mole of catechol and from 45 to 55% catechol conversion.

Ketones suitable for use in the solvent system are aliphatic (i.e. alkyl) ketones having 4 to 8 carbon atoms, including methyl ethyl ketone, diethyl ketone, methyl isobutyl ketone, and the like. The following examples illustrate the practice of the invention utilizing methyl isobutyl ketone as the organic component of the solvent system.

EXAMPLES 1A-1E

To a stirred autoclave fitted with temperature probe and liquid sampling tube the following were added for each reaction: 66.0 g of catechol (0.6 mole), 34.2 g of methallyl chloride (0.36 mole), 35.0 g of anhydrous sodium carbonate (0.33 mole), 4.14 g of anhydrous potassium carbonate (0.03 mole), 0.55 g of sodium hydrosulfite (0.003 mole), and 200 g of solvent containing methyl isobutyl ketone (MIBK) and various amounts of water. This system was purged with nitrogen, stirring was initiated, and the internal temperature was raised to 130° C. Small samples were taken from each reaction periodically and analyzed by gas chromatography to follow the progress of the etherification. When approximately 50% catechol conversion had been achieved the internal temperature was lowered to 20° C. over ten minutes.

Each crude reaction product was transferred to a one-liter, three-necked, round-bottomed flask fitted with a bottom takeoff valve, an air-driven Teflon blade stirrer, and an $N_2$ sweep. Stirring of the slurry was initiated and 150 g of deaerated distilled water was added. Slowly, in aliquots, 50 g of concentrated HCl (0.50 mole) was added over 15 minutes to neutralize the bases present. The rate of HCl addition was such that the foaming caused by $CO_2$ evolution was controllable. Stirring was continued for 15 minutes after the HCl addition was complete. The phases were allowed to separate for 15 minutes and the resulting brine (pH=2) was recovered, weighed, and analyzed for 2-methallyloxyphenol and catechol by high pressure liquid chromatography. The organic phase was recovered, weighed, and analyzed for 2-methallyloxyphenol, catechol, and by-products by gas chromatography. The conversion of catechol and selectivity to 2-methallyloxyphenol were calculated for each water level; these results are shown in Table 1 as examples 1A through 1E. Substantially shorter reaction times were achieved as water content was increased from 0.37 to 1.85 moles per mole of catechol (Examples 1A to 1D) without markedly affecting the reaction selectivity to 2-methallyloxyphenol. When the water/catechol ratio was increased beyond 1.85 to 3.7 (Example 1E) the shorter reaction time was accompanied by lower, less desirable selectivity.

EXAMPLES 2A-2H

These examples were run in the same manner as Examples 1A-1E except that (1) the base employed was sodium carbonate rather than a mixture of sodium and potassium carbonate and (2) in Examples 2D and 2E 37.1 g (0.39 mole) of methallyl chloride was employed and in Examples 2F to 2H 39.9 g (0.42 moles) of methallyl chloride was employed. The results, shown in Table 1, again show that reaction time continues to improve with increasing water content, but high selectivity is lost when a high water to catechol ratio is utilized.

TABLE 1

| Example | Water/Catechol Ratio (Mole) | Reaction[1] Time (Min) | Catechol Conversion (%) | Selectivity (%) |
|---|---|---|---|---|
| 1A | 0.37 | 175 (175) | 45.8 | 95.6 |
| 1B | 1.11 | 145 (140) | 46.1 | 95.1 |
| 1C | 1.48 | 145 (110) | 47.2 | 93.8 |
| 1D | 1.85 | 145 (110) | 50.4 | 92.4 |
| 1E | 3.70 | 115 (80) | 46.8 | 90.4 |
| 2A | 0 | 170 (150) | 45.0 | 92.0 |
| 2B | 1.48 | 175 (135) | 48.5 | 92.3 |
| 2C | 1.85 | 145 (120) | 48.8 | 88.6 |
| 2D | 1.48 | 115 (115) | 45.6 | 93.6 |
| 2E | 1.85 | 115 (115) | 46.6 | 94.3 |
| 2F | 1.85 | 115 (115) | 50.9 | 89.2 |
| 2G | 2.78 | 85 (85) | 50.3 | 88.2 |
| 2H | 3.70 | 85 (75) | 50.4 | 86.5 |

[1]Times without parentheses are actual run times, including a 25-30 minute warm-up period. These times generally exceed the period needed to achieve maximum yields. Optimum times appear in parentheses and were calculated from plots of reaction time versus area percent 2-methallyloxyphenol based on gas chromatographic analysis of the reaction mixture.

We claim:

1. In a process for preparing 2-methallyloxyphenol by reacting catechol with methallyl chloride at a temperature in the range of 70° C. to 150° C. in the presence of one or more bases selected from the group consisting of alkali metal carbonates, alkali metal bicarbonates, alkaline earth carbonates, and alkaline earth bicarbonates, said reaction being conducted without an etherification catalyst in a solvent system consisting of water and an aliphatic ketone having 4 to 8 carbon atoms, using from 0.55 to 0.75 moles of methallyl chloride per mole of catechol, the improvement comprising using a molar ratio of 0.3 to 1.9 moles of water per mole of catechol and conducting the reaction for a period of 1 to 3 hours.

2. The process of claim 1 wherein the ketone employed in the solvent system is methyl isobutyl ketone.

3. The process of claim 1 wherein the base is an alkali metal carbonate selected from sodium carbonate, and a mixture of sodium and potassium carbonates.

4. The process of claim 1 wherein sodium and potassium carbonate are employed in a molar ratio in the range of 5:1 to 20:1.

* * * * *